US00PP37191P2

(12) United States Plant Patent
Hofmann

(10) Patent No.: US PP37,191 P2
(45) Date of Patent: Jan. 6, 2026

(54) ***PETUNIA* PLANT NAMED 'INPETBOAUX'**

(50) Latin Name: ***Petunia* X *hybrida***
Varietal Denomination: INPETBOAUX

(71) Applicant: Birgit Hofmann, Rudesheim am Rhein (DE)

(72) Inventor: Birgit Hofmann, Rudesheim am Rhein (DE)

(73) Assignee: INNOVAPLANT ZIERPFLANZEN GMBH & Co. KG, Gensingen (DE)

( * ) Notice: Subject to any disclaimer, the term of this patent is extended or adjusted under 35 U.S.C. 154(b) by 0 days.

(21) Appl. No.: 19/261,869

(22) Filed: Jul. 7, 2025

(51) Int. Cl.
*A01H 5/02* (2018.01)
*A01H 6/82* (2018.01)

(52) U.S. Cl.
USPC ..... Plt./356.17
CPC ..... *A01H 6/824* (2018.05)

(58) Field of Classification Search
USPC ..... Plt./356.17, 356.19
CPC ..... A01H 5/02
See application file for complete search history.

*Primary Examiner* — Kent L Bell
(74) *Attorney, Agent, or Firm* — C. Anne Whealy

(57) ABSTRACT

A new and distinct *Petunia* plant named 'INPETBOAUX', characterized by its upright to outwardly spreading and mounding plant habit to eventually trailing with subsequent development; moderately vigorous growth habit and rapid growth rate; freely branching habit; dense and bushy plant form; early and freely flowering habit; single-type flowers that are light pale purple in color with contrasting dark purple venation and centers; flowers that maintain color and resist fading; and good container and garden performance.

2 Drawing Sheets

Figure 1:
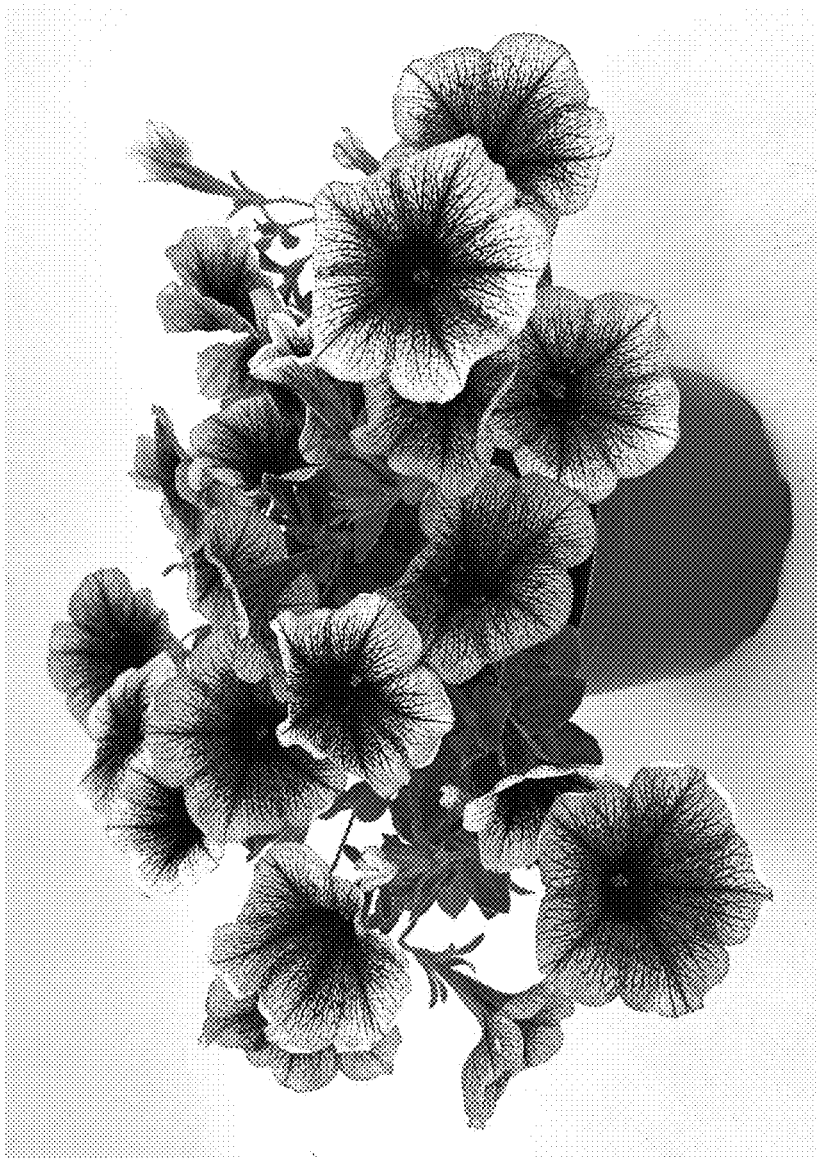

Botanical designation: *Petunia* X *hybrida.*
Cultivar denomination: 'INPETBOAUX'.

BACKGROUND OF THE INVENTION

The present invention relates to a new and distinct cultivar of *Petunia* plant, botanically known as *Petunia* X *hybrida* and hereinafter referred to by the name 'INPETBOAUX'.

The new *Petunia* plant is a product of a planned breeding program conducted by the Inventor in Johannesburg, South Africa and Heidesheim, Germany. The objective of the breeding program is to create new moderately vigorous to vigorous, freely-branching and uniformly mounding *Petunia* plants with early and freely flowering habit, attractive flowers and good garden performance.

The new *Petunia* plant originated from a cross-pollination made by the Inventor in November 2021 in Johannesburg, South Africa of a proprietary selection of *Petunia* X *hybrida* identified as code number Pt20-5570-3, not patented, as the female, or seed, parent with a proprietary selection of *Petunia* X *hybrida* identified as code number Pt20-5565-3, not patented, as the male, or pollen, parent. The new *Petunia* plant was discovered and selected by the Inventor as a single flowering plant within the progeny of the stated cross-pollination in a controlled greenhouse environment in Heidesheim, Germany in May 2022.

Asexual reproduction of the new *Petunia* plant by vegetative terminal cuttings in a controlled greenhouse environment in Heidesheim, Germany since June 2022 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'INPETBOAUX'. These characteristics in combination distinguish 'INPETBOAUX' as a new and distinct *Petunia* plant:

1. Upright to outwardly spreading and mounding plant habit to eventually trailing with subsequent development.
2. Moderately vigorous growth habit and rapid growth rate.
3. Freely branching habit; dense and bushy plant form.
4. Early and freely flowering habit.
5. Single-type flowers that are light pale purple in color with contrasting dark purple venation and centers.
6. Flowers that maintain their color and resist fading.
7. Good container and garden performance.

Plants of the new *Petunia* can be compared to plants of the female parent selection. In side-by-side comparisons, plants of the new *Petunia* differ primarily from plants of the female parent selection in the following characteristics:

1. Plants of the new *Petunia* are not as upright as and are more mounding and trailing than plants of the female parent selection.
2. Plants of the new *Petunia* are more tolerant to rain and high light levels than plants of the female parent selection.

Plants of the new *Petunia* can be compared to plants of the male parent selection. In side-by-side comparisons, plants of the new *Petunia* differ primarily from plants of the male parent selection in the following characteristics:

1. Plants of the new *Petunia* are more mounding and trailing than plants of the male parent selection.

2. Plants of the new *Petunia* are stronger and more vigorous than plants of the male parent selection.
3. Plants of the new *Petunia* have larger and flatter flowers than plants of the male parent selection.
4. Flowers of plants of the new *Petunia* are light pale purple in color with contrasting dark purple venation and centers whereas flowers of plants of the male parent selection are white in color with lilac-colored venation.

Plants of the new *Petunia* can be compared to plants of *Petunia* X *hybrida* 'Lanbor', disclosed in U.S. Plant Pat. No. 16,144. In side-by-side comparisons, plants of the new *Petunia* differ primarily from plants of 'Lanbor' in the following characteristics:

1. Plants of the new *Petunia* are more mounding than and not as outwardly spreading as plants of 'Lanbor'.
2. Plants of the new *Petunia* are more freely branching and are bushier and denser than plants of 'Lanbor'.
3. Plants of the new *Petunia* are more freely flowering than plants of 'Lanbor'.
4. Flowers of plants of the new *Petunia* have narrow white-colored marginal edges whereas flowers of plants of 'Lanbor' do not have white-colored marginal edges.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet (FIG. 1) is a side perspective view of a typical flowering plant of 'INPETBOAUX' grown in a container.

Figure 2:
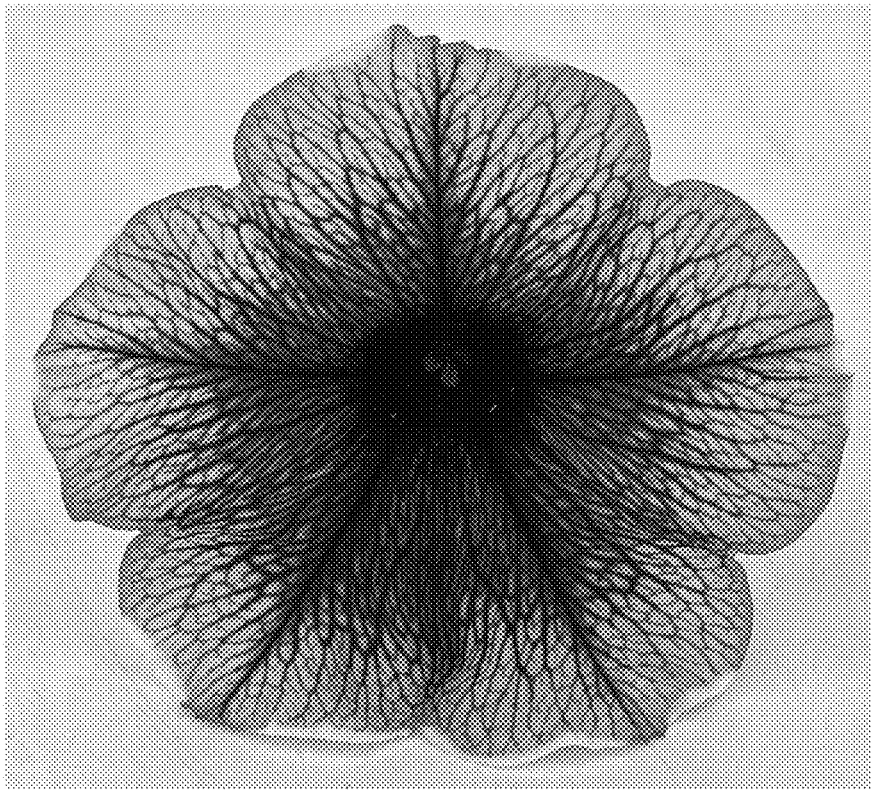

The photograph on the second sheet (FIG. 2) is a close-up view of a typical flower of 'INPETBOAUX'.

DETAILED BOTANICAL DESCRIPTION

The aforementioned photographs and following observations and measurements describe plants grown during the late spring and early summer in 4.25-inch (813-ml) containers in a glass-covered greenhouse in Loudon, New Hampshire and under cultural practices typical of commercial *Petunia* production. During the production of the plants, day and night temperatures ranged from 20° C. to 25° C. and night temperatures ranged from 15° C. to 18° C. Plants were eight weeks from planting three-week old rooted young plants when the photographs and description were taken. Plants were pinched one time at the time of planting. In the following description, color references are made to The Royal Horticultural Society Colour Chart, 2015 Edition, except where general terms of ordinary dictionary significance are used.

Botanical classification: *Petunia* X *hybrida* 'INPETBOAUX'.

Parentage:

*Female, or seed, parent*.—Proprietary selection of *Petunia* X *hybrida* identified as code number Pt20-5570-3, not patented.

*Male, or pollen, parent*.—Proprietary selection of *Petunia* X *hybrida* identified as code number Pt20-5565-3, not patented.

Propagation:

*Type*.—Terminal vegetative cuttings.

*Time to initiate roots, summer*.—About two weeks at temperatures about 22° C.

*Time to initiate roots, winter*.—About 18 days at temperatures about 18° C.

*Time to produce a rooted plant, summer*.—About 20 days at temperatures about 22° C.

*Time to produce a rooted plant, winter*.—About 25 days at temperatures about 18° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Upright to outwardly spreading and mounding to eventually trailing plant habit; freely branching habit with about six to seven primary lateral branches with secondary laterals developing potentially at every node, dense and bushy plant form; pinching enhances development of lateral branches; moderately vigorous growth habit and rapid growth rate.

*Plant height*.—About 13.5 cm to 15 cm.

*Plant diameter* (*area of spread*).—About 25 cm to 27 cm.

*Lateral branches*.—Length: About 13 cm to 15 cm. Diameter: About 4 mm to 5 mm. Internode length: About 9 mm to 12 mm. Strength: Strong; flexible, not brittle. Aspect: Initially upright then outwardly spreading to eventually trailing. Texture and luster: Densely pubescent; pubescence, fine; slightly glossy to matte. Color, developing and developed: Close to 146A.

Leaf description:

*Arrangement*.—Alternate before flowering; opposite after flowers develop; leaves simple.

*Length, largest leaves*.—About 3.5 cm to 4.1 cm.

*Width, largest leaves*.—About 3.25 cm to 3.5 cm.

*Shape*.—Ovate to elliptic.

*Apex*.—Acute.

*Base*.—Obtuse with cuneate tendencies.

*Margin*.—Entire, not undulate.

*Texture and luster, upper and lower surfaces*.—Sparsely to moderately pubescent, pubescence, minute; matte to slightly glossy.

*Venation pattern*.—Pinnate, arcuate.

*Color*.—Developing leaves, upper surface: Close to 146A. Developing leaves, lower surface: Close to 146A to 146B. Fully developed leaves, upper surface: Close to 147A; venation, close to between 146A and 147A. Fully developed leaves, lower surface: Close to 146A; venation, close to 146A.

*Petioles*.—Length: About 6 mm to 8 mm. Diameter: About 3.5 mm to 4 mm. Strength: Strong, flexible. Texture and luster, upper and lower surfaces: Moderately pubescent; semi-glossy. Color, upper surface: Close to 146A and along the margins, close to 147A. Color, lower surface: Close to 146A.

Flower description:

*Flower type and flowering habit*.—Single terminal and axillary salverform flowers; flowers face mostly upward to outwardly; freely flowering habit with about 45 flower buds, developing flowers and open flowers per plant at one time.

*Natural flowering season*.—Long day responsive; long flowering period, plants flower from early spring until frost in the autumn, flowering continuous during this period; early flowering habit, depending on temperature, plants begin flowering about 24 days after planting rooted young plants.

*Flower longevity on the plant*.—Depending on temperature, individual flowers last about five to seven days; petals not persistent, and sepals, persistent.

*Fragrance*.—None detected.

*Flower buds, just before petals part*.—Length: About 2 cm. Diameter: About 5 mm. Shape: Oblong, elongate. Texture and luster: Pubescent; slightly glossy to matte. Color, immature sepals, lower surface: Close to between 144A and 146A. Color, immature petals, lower surface: Close to N144A.

*Flower diameter*.—About 4.5 cm to 5 cm.

*Flower depth* (*height*).—About 4.5 cm to 4.75 cm.

*Throat diameter*.—About 9 mm to 11 mm.

*Tube length*.—About 3.5 cm to 3.75 cm.

*Tube diameter, distally*.—About 9.5 mm to 11.5 mm.

*Tube diameter, proximally*.—About 3 mm to 4 mm.

*Petals*.—Quantity and arrangement: Five petals fused in a single salverform whorl. Petal lobe length (from throat): About 1.75 cm to 2.25 cm. Petal lobe width: About 2.1 cm to 2.25 cm. Petal lobe shape: Roughly spatulate. Petal lobe apex: Broadly obtuse with acute apex. Petal lobe margin: Entire; moderately undulate. Petal lobe texture and luster, upper surface: Smooth, glabrous; velvety; matte. Petal lobe texture and luster, lower surface: Slightly pubescent; slightly glossy. Throat texture and luster: Smooth, glabrous; slightly glossy. Tube texture and luster: Moderately pubescent; matte. Color: When opening and fully opened, upper surface: Ground color, close to 76D; venation and towards the throat, close to N81A; narrow marginal edges, close to NN155D; colors do not change with subsequent development. When opening and fully opened, lower surface: Close to 76C to 76D; midvein, close to 146A and lateral venation, close to 76C to 76D; colors do not change with subsequent development. Flower throat (inside): Close to between 79A and N79A; venation, close to between 79A and N79A. Flower tube (outside): Close to 77A to 77B; venation, close to 146A.

*Sepals*.—Quantity and arrangement: Typically five sepals fused towards the base in a single star-shaped whorl; sepals flaring and arching outwardly. Calyx length: About 1.8 cm to 2 cm. Calyx diameter: About 1.8 cm to 2 cm. Length: About 1.8 cm to 2 cm. Width: About 2 mm to 3 mm. Shape: Narrowly oblong to linear. Apex: Obtuse. Margin: Entire. Texture and luster, upper surface: Sparsely to moderately pubescent; pubescence, fine; matte. Texture and luster, lower surface: Moderately pubescent; pubescence, fine; matte. Color, upper and lower surfaces: Close to 146A; towards the base, close to 146B.

*Peduncles, terminal flowers*.—Length: About 2.5 cm to 2.75 cm. Width: About 1 mm. Strength: Moderately strong to strong; wiry and flexible, not brittle. Angle: About 30° to 45° from the stem axis. Texture and luster: Moderately to densely pubescent; matte to slightly glossy. Color: Close to 144A.

*Reproductive organs*.—Stamens: Quantity per flower: About five. Filament length: About 2 cm to 2.4 cm. Filament color: Close to 157D. Anther length: About 1 mm. Anther shape: Bi-lobed. Anther color: Close to 97A. Pollen amount: None observed. Pistils: Quantity per flower: One. Pistil length: About 2.1 cm to 2.3 cm. Style length: About 1.8 cm to 2 cm. Style color: Close to 144C. Stigma diameter: About 1.5 mm to 2 mm. Stigma shape: Rounded. Stigma color: Close to 96A. Ovary color: Close to 145C to 145D.

*Seeds and fruits*.—To date, seed and fruit development has not been observed on plants of the new *Petunia*.

Pathogen & pest resistance: To date, plants of the new *Petunia* have not been noted to be resistant to pathogens or pests common to *Petunia* plants.

Garden performance: Plants of the new *Petunia* have been observed to have good garden performance and have been observed to tolerate rain, wind, high light conditions and temperatures ranging from about 4° C. to about 40° C.

It is claimed:

1. A new and distinct *Petunia* plant named 'INPETBOAUX' as herein illustrated and described.

* * * * *